US00PP27723P3

(12) United States Plant Patent
Verschoor

(10) Patent No.: US PP27,723 P3
(45) Date of Patent: Feb. 28, 2017

(54) ***PHLOX* PLANT NAMED 'KAZI14750'**

(50) Latin Name: *Phlox drummondii*
Varietal Denomination: KAZI14750

(71) Applicant: Klemm+Sohn GmbH & Co. KG, Stuttgart (DE)

(72) Inventor: Katrin Verschoor, Klaaswaal (NL)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 14/757,257

(22) Filed: Dec. 10, 2015

(65) Prior Publication Data

US 2017/0020051 P1 Jan. 19, 2017

(30) Foreign Application Priority Data

Jul. 16, 2015 (QZ) ..... PBR 2015/1685

(51) Int. Cl.
*A01H 5/02* (2006.01)

(52) U.S. Cl.
USPC ..... Plt./320

(58) Field of Classification Search
USPC ..... Plt./320
See application file for complete search history.

*Primary Examiner* — Annette Para
(74) *Attorney, Agent, or Firm* — Barbara Campbell; Bethany R. Roahrig; Cochran Freund & Young, LLC

(57) ABSTRACT

A new *phlox* plant particularly distinguished by pink flowers and a compact, upright to outwardly spreading and mounding plant and growth habit, is disclosed.

1 Drawing Sheet

Genus and species: *Phlox drummondii.*
Variety denomination: 'KAZI14750'.

CROSS REFERENCE TO RELATED APPLICATIONS

This application claims priority to and the benefit of European Community Plant Variety Rights Application No. 2015/1685, filed Jul. 16, 2015, the entire contents of which are incorporated herein by reference for all purposes.

BACKGROUND OF THE NEW PLANT

The present invention comprises a new and distinct variety of *phlox*, botanically known as *Phlox drummondii* and hereinafter referred to by the variety name 'KAZI14750'. 'KAZI14750' originated from a controlled-cross in Mijnsheerenland, The Netherlands in summer 2007 between the proprietary female *phlox* variety 'Surphlox 1' (unpatented) and the proprietary male *phlox* variety 'Surphlox 2' (unpatented). Seeds from the cross were obtained and plants were grown for evaluation.

A single plant was selected in August 2008 and subsequently named 'KAZI14750'. In August 2008, 'KAZI14750' was first vegetatively propagated by stem cuttings in Mijnsheerenland, The Netherlands and from September 2008 in Stuttgart, Germany. 'KAZI14750' was found to reproduce true to type in successive generations of asexual propagation via stem cuttings in Stuttgart, Germany.

SUMMARY

The following are the most outstanding and distinguishing characteristics of this new variety when grown under normal horticultural practices in Stuttgart, Germany.

1. Pink flowers; and
2. A compact, upright to outwardly spreading and mounding plant and growth habit.

DESCRIPTION OF THE PHOTOGRAPH

This new *phlox* plant is illustrated by the accompanying photograph which shows an overall view of the whole plant. The photograph is of an approximately 12-week-old plant grown in Stuttgart, Germany under greenhouse conditions in June 2012.

The colors shown are as true as can be reasonably obtained by conventional photographic procedures.

DESCRIPTION OF THE NEW VARIETY

The following detailed descriptions set forth the distinctive characteristics of 'KAZI14750'. The data which define these characteristics were collected from asexual reproductions carried out in Stuttgart, Germany. Data was collected on 10-week-old plants after potting in the greenhouse in Stuttgart, Germany. Color references are to The R.H.S. Colour Chart of The Royal Horticultural Society of London (R.H.S.), 5$^{th}$ edition (2007).

Classification:
- *Family.*—Polemoniaceae.
- *Botanical.*—*Phlox drummondii.*
- *Designation.*—'KAZI14750'.

Parentage:
- *Female parent.*—The proprietary female *phlox* variety 'Surphlox 1' (unpatented).
- *Male parent.*—The proprietary male *phlox* variety 'Surphlox 2' (unpatented).

Propagation:
- *Type.*—Stem cuttings.
- *Time to initiate roots, summer.*—About five days at temperatures of about 20 degrees C.
- *Time to initiate roots, winter.*—About seven days at temperatures of about 20 degrees C.
- *Time to produce a rooted plant, summer.*—About three weeks at temperatures of about 20 degrees C.

*Time to produce a rooted plant, winter.*—About four weeks at temperatures of about 20 degrees C.
*Root description.*—Fine, fibrous, white in color.
*Rooting habit.*—Freely branching, dense.

Plant:
*Plant and growth habit.*—Compact, upright to outwardly spreading and mounding.
*Plant height.*—14.0 cm.
*Plant width (spread).*—17.0 cm.

Lateral branches or stems:
*Length.*—12.0 cm.
*Diameter.*—3.0 mm.
*Internode length.*—2.0 cm.
*Strength.*—Strong.
*Thickness at middle third.*—Thin.
*Texture.*—Pubescent.
*Color.*—RHS 145A.
*Anthocyanin.*—Absent.

Leaves:
*Arrangement.*—Opposite, simple.
*Length.*—3.6 cm.
*Width.*—1.6 cm.
*Shape.*—Elliptic.
*Apex.*—Apiculate (ending abruptly in a small distinct point).
*Base.*—Truncate to obtuse.
*Margin.*—Finely serrate.
*Texture (both upper and lower surfaces).*—Smooth, glabrous.
*Venation pattern.*—Pinnate.
*Color.*—Developing leaves: Upper surface: RHS 144A. Lower surface: RHS 143C. Fully expanded (mature) leaves: Upper surface: RHS 146A. Lower surface: RHS 147B. Venation: RHS 145A.
*Position of broadest part of leaf.*—Towards apex.
*Shape in cross section.*—Concave.
*Leaf variegation.*—Absent.
*Anthocyanin coloration on upper surface.*—Absent.
*Undulation of margin.*—Absent or weak.

Petiole:
*Length.*—1.0 mm.
*Diameter.*—1.0 mm.
*Texture (both upper and lower surfaces).*—Smooth, glabrous.
*Color.*—Upper surface: RHS N144B. Lower surface: RHS 145C.

Flower:
*Flower type and flowering habit.*—Single rotate salverform flowers arranged in small panicles.
*Quantity of flowers per inflorescence.*—Freely flowering habit with about four flowers per inflorescence.
*Fragrance.*—Moderately fragrant, sweet, pleasant.
*Natural flowering season.*—Continuously flowering from summer to late summer in Germany.
*Postproduction longevity.*—Flowers last about three to four days on the plant, flowers not persistent.
*Flower buds.*—Height: 8.0 mm. Diameter: 3.0 mm. Shape: Narrowly obovate. Color: RHS 182C.
*Inflorescence height.*—3.0 cm.
*Inflorescence diameter.*—6.5 cm.
*Flower diameter.*—2.5 cm.
*Flower depth.*—1.3 cm.
*Flower throat diameter.*—3.0 mm.
*Flower tube length.*—1.2 cm.
*Flower tube diameter, at the base.*—1.5 mm.
*Perianth.*—Present, not achlamydeous.

Petals:
*Quantity per flower and arrangement.*—Five petals arranged in a single whorl and fused at the base into a narrow tube.
*Length from throat.*—1.0 cm.
*Width.*—1.1 cm.
*Shape.*—Spatulate.
*Apex.*—Rounded.
*Margin.*—Entire.
*Texture (both upper and lower surfaces).*—Smooth, glabrous.
*Texture of throat.*—Smooth, glabrous.
*Texture of tube.*—Smooth, glabrous.
*Color.*—Developing petals: Upper surface: RHS 65A with RHS 59A eyes. Lower surface: RHS 69C. Fully expanded petals: Upper surface: RHS 68A with RHS 59A eyes. Lower surface: RHS 69B. Flower throat: RHS 59A. Flower tube: RHS 60B.

Sepals:
*Width of calyx.*—0.3 cm.
*Length of calyx.*—1.4 cm.
*Quantity per flower and arrangement.*—5.
*Length.*—1.0 cm.
*Width.*—1.0 mm.
*Shape.*—Lanceolate.
*Apex.*—Narrowly apiculate.
*Margin.*—Entire.
*Texture (both upper and lower surfaces).*—Smooth, glabrous.
*Color.*—Upper surface: RHS 146B. Lower surface: RHS 146C.
*Anthocyanin coloration.*—Absent.

Peduncles:
*Length.*—2.0 cm.
*Diameter.*—3.0 mm.
*Angle.*—Upright.
*Strength.*—Strong.
*Texture.*—Smooth, glabrous.
*Color.*—RHS 145A.

Pedicels:
*Length.*—1.3 cm.
*Diameter.*—1.0 mm.
*Angle.*—30 degrees from the peduncle axis.
*Strength.*—Strong.
*Texture.*—Smooth, glabrous.
*Color.*—RHS 145A.
*Anthocyanin.*—Absent.

Reproductive organs:
*Stamens.*—Quantity per flower: 5. Filament length: 5.0 mm. Filament color: RHS 157B. Anther shape: Oblong. Anther length: 2.0 mm. Anther color: RHS 14A. Pollen amount: Abundant. Pollen color: RHS 14A.
*Pistils.*—Quantity per flower: 1. Pistil length: 4.0 mm. Stigma shape: Bi-parted. Stigma color: RHS 3B. Style length: 2.0 mm. Style color: RHS 149C. Ovary color: RHS 144A.

Fruit and seed set: Seeds and fruit development have not been observed.

Disease and pest/insect resistance: None observed.

COMPARISON WITH PARENTAL LINES AND KNOWN VARIETY

'KAZI14750' is distinguished from its parents as described in Table 1:

TABLE 1

| Comparison with Parental Varieties | | | |
|---|---|---|---|
| Trait | 'KAZI14750' | Female parent 'Surphlox 1' | Male parent 'Surphlox 2' |
| Flower color | Pink | White | Dark pink |
| Habit | Compact, upright to outwardly spreading and mounding plant and growth habit | Upright, medium-compact | Semi-trailing, compact |

'KAZI14750' can be compared to the commercial variety 'Phloxy Lady Pink' (patent status unknown). Differences between the two varieties are described in Table 2:

TABLE 2

| Comparison with Similar Variety | | |
|---|---|---|
| Trait | 'KAZI14750' | Commercial line 'Phloxy Lady Pink' |
| Habit | Compact, upright to outwardly spreading and mounding plant and growth habit | Strong, upright |

I claim:

1. A new and distinct variety of *phlox* plant named 'KAZI14750' as illustrated and described herein.

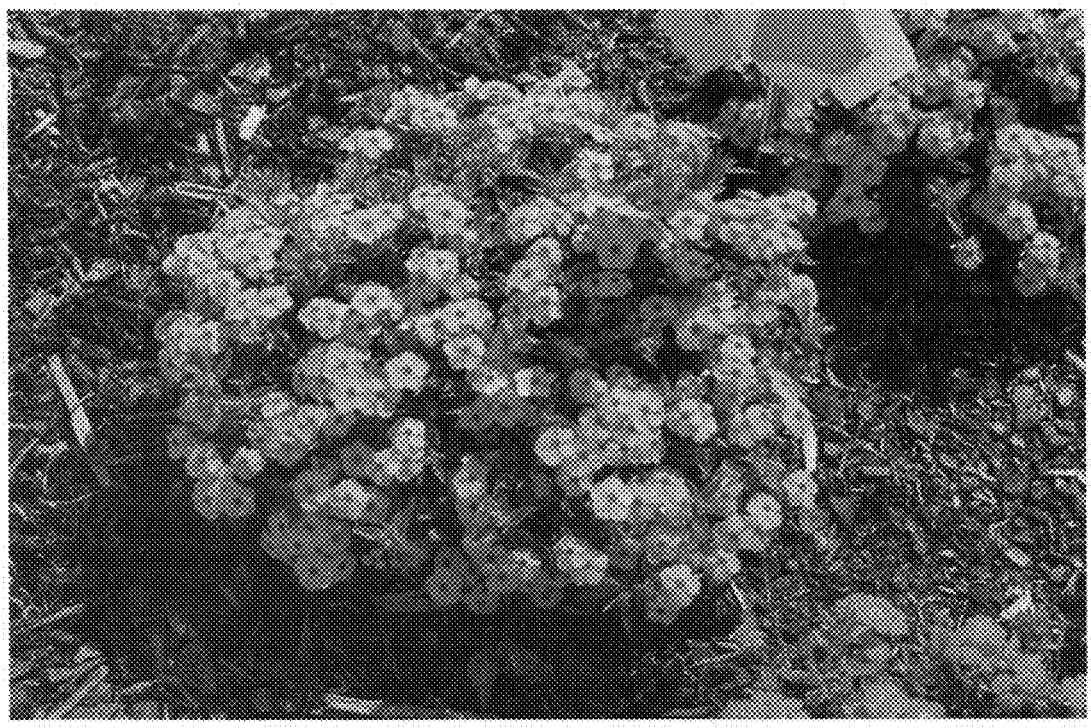

* * * * *